United States Patent [19]
Schaumann et al.

[11] Patent Number: 5,735,865
[45] Date of Patent: Apr. 7, 1998

[54] INSTRUMENT FOR ENDOSCOPIC THERAPY

[75] Inventors: Uwe Schaumann, Villingen-Schwenningen; Helmut Heckele, Knittlingen; Friederich Hähnle, Bretten, all of Germany

[73] Assignee: Richard Wolf GmbH, Knittlingen, Germany

[21] Appl. No.: 758,532

[22] Filed: Nov. 29, 1996

[30]    Foreign Application Priority Data

Dec. 19, 1995 [DE] Germany .......... 195 47 383.3

[51] Int. Cl.⁶ .................................................. A61B 17/32
[52] U.S. Cl. ............................................ 606/167; 600/101
[58] Field of Search .................. 606/1, 159, 167–185; 600/101

[56]    References Cited
U.S. PATENT DOCUMENTS 5,089,000  2/1992  Agee et al. .
5,242,460  9/1993  Klein et al. .............. 606/180
5,282,816  2/1994  Miller et al. ............. 606/167
5,306,284  4/1994  Agee et al. .

FOREIGN PATENT DOCUMENTS

2737014 A1  3/1979  Germany .
0552980 A1  7/1993  Germany .
WO 93/10704  6/1993  WIPO .
WO 93/12725  7/1993  WIPO .

*Primary Examiner*—Glenn K. Dawson
*Attorney, Agent, or Firm*—Panitch Schwarze Jacobs & Nadel, P.C.

[57]    ABSTRACT

The invention relates to an instrument for endoscopic therapy. A cutting tool including a rigid tubular shank is so guided within a tubular longitudinally slotted instrument shank having an essentially oval inner cross section, that the cutting tool may be tilted out of the axis of the instrument shank, whereby a cutter of the cutting tool penetrates the longitudinal slit of the instrument shank and projects beyond the diameter of the instrument shank. In this way by varying the tilting angle of the cutting tool the cutting depth of the cutting tool may be delicately set.

6 Claims, 3 Drawing Sheets

INSTRUMENT FOR ENDOSCOPIC THERAPY

BACKGROUND OF THE INVENTION

The invention relates to an instrument for endoscopic therapy, in particular for therapy of carpal tunnel syndrome, whereby the instrument comprises a shank tube longitudinally slotted at least over part of its length, a cutting tool having a cutter and being displaceable in the longitudinal direction of the shank tube and within said shank tube, and an observation optic.

DESCRIPTION OF THE PRIOR ART

Such an instrument is for example deduced from WO 93/10704. This instrument provides for the therapy of the carpal tunnel syndrome and is applied in combination with the so called two- portal procedure in which two openings are formed in the hand which serve the instrument as an entry portal or an exit portal. The instrument essentially comprises a probe which is provided with a longitudinal slit and according to the procedure, is introduced into the entry portal and is led out from the exit portal. For observing the operation site, a video endoscope may be pushed into the distal end of the probe which projects out of the entry portal. As such, the observation may be effected during the operation, carried out from the proximal side of the probe, by way of a suitable scalpel type instrument introduced from here, whereby in any case the operator undertakes the operation and a second person undertakes the guiding of the video arthroscope.

An instrument for application with the so called one portal-procedure is disclosed in EP-A-0552980. This instrument comprises a hollow probe which is closed at its distal end and provided with a longitudinal recess. Into this hollow probe from its proximal end, an optic for observing the operation region may be inserted. For the therapy of carpal tunnel syndrome, a suitable surgical instrument such as a scalpel may be introduced into the longitudinal recess of the probe and the operation with this instrument may be observed via the endoscope optic. This intrument too only lends itself to operate optimally when two operators are employed.

With instruments according to this state of the art, is must be noted that it is generally of a disadvantage that it is constantly necessary to have two operators for carrying out the operation. Moreover, with regard to the two-portal procedure, the requirement of the arrangement of two incisions must be emphasised, these incisions causing an additional traumatic stress for the patient. Similar problems occur when instruments of this type are for example applied in the therapy of radialis paralysis.

An instrumentation for carrying out the previously mentioned one-portal technology according to the preamble is likewise known from the U.S. Pat. No. 5,306,284, in which, in particular with the introduction procedure, the knife for severing the ligament is hidden in the distal tip of the instrument in order to prevent inadvertent cuts on introduction or for use in the case that a diagnosis only is to be carried out.

For carrying out the severing of the ligament, the cutting knife, foldable out of the distal tip of the instrument via several links, is folded out of the instrument shank and by pulling back the complete instrument the necessary cut is made. Apart from the tendency for breakage of the multiple link solution and the complicated and costly design of this solution, it must be noted that there exists the further disadvantage in that only a small shank opening is provided and thus the endoscopic field of view is already quite limited. With the knife folded out, i.e. in the working position, the field of view with this solution becomes limited even further.

From WO 93/12725 an instrument for the therapy of carpal tunnel syndrome is likewise known. This instrument comprises essentially of a shank, the distal end of which being bent and extended beyond its diameter. An endoscope or an endoscope optic carrying a cutting tool at its distal end is guided within this shank. This cutting tool can be adapted to the previously mentioned bent region and the cutter faces the proximal direction. On introduction of the shank into the carpal tunnel, the endoscope or the endoscope optic is somewhat pulled back out of the shank, and the cutting tool is located protected behind the bent distal part of the shank. With this instrumentation too, the severing of the ligament is effected with a cutting path from the distal to the proximal direction, in which the endocope with the knife attached thereto is pulled out of the sleeve or together with the sleeve out of the carpal tunnel.

The adaptation of the cutting tool to the bending of the shank is effected in that the connection of the cutting tool to the endoscope or in another embodiment, the connection to the proximal end, is kept quite thin, by which means there is a type of spring effect. This design however has the disadvantage that due to this spring effect, the cutting path is relatively unstable. A further disadvantage of this and the other previous described instruments of the state of the art can be seen in that the cutting depth cannot be varied. Moreover, the measure for protecting against any inadvertent cutting, that is, extending the distal end of the shank beyond its diameter, leads to a not inconsiderable traumatization of the surrounding tissue. Therefore, as a whole, this instrumentation, particularly due to the limited space available in the operating region for which these instruments are intended, is to be regarded as disadvantageous.

SUMMARY OF THE INVENTION

It is therefore the object of the invention to improve an instrument for diagnosis or therapy in particular of carpal tunnel syndrome, such that an inadvertent cutting of tissue on introduction of the instrument or on diagnosis is avoided and furthermore a stable cutting effect is achieved, whereby in particular, the cutting depth may be variably set by the operator in a tactile manner. Furthermore, at the same time, a reduced constructional height or a reduced diameter compared to the instruments of the prior art is to be achieved.

This object is achieved with an instrument of the previously mentioned type in that means are provided for tilting the cutting tool for cutting within the shank tube relative to the longitudinal axis of said shank tube, the cutter of the cutting tool in the tilted condition penetrating the longitudinal slit of the shank tube and projecting beyond the outer diameter of the shank tube.

An instrument constructed in such a manner may be safely operated by the operator with one hand, whereby it is ensured that on introduction of the completed instrument, an inadvertent cutting is impossible and if a cutting effect is to be achieved then this may be effected delicately because of the tactile manner.

Due to the design of the complete instrument from easily detachable parts connectable to one another, an easy disassembly of the instrument into individual parts is made possible, these parts then being easily cleaned and sterilized.

Further advantageous features of the instrument according to the invention are specified in the dependent claims.

BRIEF DESCRIPTION OF THE DRAWINGS

By way of example, the invention is hereinafter described in more detail by way of drawings. These show:

FIG. 1 a view of the complete instrument according to the invention with a protected cutting tool, FIGS. 2a to 2c views of the individual instrument parts which may be releasably connected to one another, FIG. 2a showing an optic, FIG. 2b the cutting tool and FIG. 2c the longitudinally slotted shank, FIG. 2d a section through the tube of the cutting tool of a first embodiment of the cutting tool taken along the D according to FIG. 2b, FIG. 2e a section of a cutting tool tube of a further advantageous embodiment form corresponding to line D—D according to FIG. 2d, FIG. 3a a view of the complete instrument according to the invention, whereby the cutting tool tube and the optic are coupled and detached from the longitudinally slotted instrument shank, in the non-tilted position, FIG. 3b the instrument according to the invention corresponding to FIG. 3a in the tilted position, FIG. 4a the shank according to FIG. 2c, FIG. 4b a section taken along line B—B according to FIG. 4a and FIG. 5 a horizontal projection of the shank in the direction V according to FIG. 4a.

DETAILED DESCRIPTION OF THE INVENTION

Figure 1:
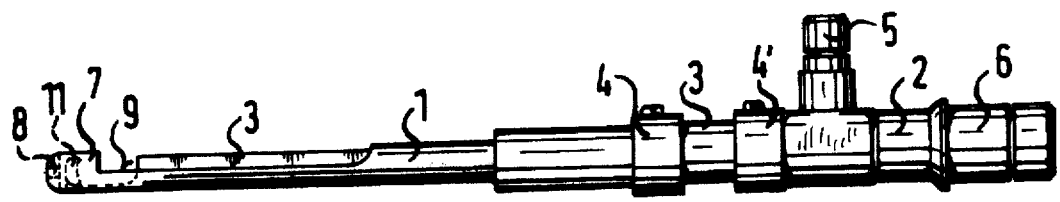

FIG. 1 shows the complete instrument according to the invention in a schematic lateral view, the instrument comprising a tubular instrument shank 1 which at the proximal side comprises a lock 4 known per se, e.g. a conical lock.

The instrument shank 1 is atraumatically rounded at its distal end 7 where it comprises a coaxial bore 8 as can be recognised more clearly from FIG. 2c, to be discussed hereinafter. The instrument shank 1 further comprises a longitudinal slit 9 over a defined section of length running to, and ending shortly before the shank's distal end 7. A cutting tool 3 may be releasably detached to the instrument shank 1 on the proximal side via the coupling mechanism of the lock 4.

The design on the lock 4, known per se, provides for the instrument shank 1 and the cutting tool 3 to be connectable to one another with a defined radial arrangement and in a rotationally secure manner. As already mentioned, the lock 4 may be a conical lock known per se, and then the cutting tool 3 comprises, as shown in FIG. 2b, a corresponding connection cone 4".

Figure 2A:
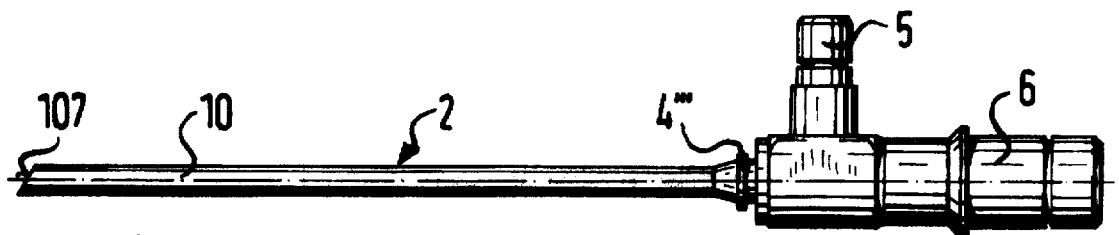

At its proximal end, the cutting tool 3 also comprises a lock 4' which for its part cooperates with a correspondingly formed part 4'" of an optic 2 (cf., FIG. 2a). By way of this lock 4', the optic 2 is fixed to the cutting tool 3 which is releasably and rotationally securely attached to the instrument shank 1, this being likewise in a releasable, rotationally secure manner and with a defined radial arrangement. The optic 2 represented only by way of example according to FIG. 1 or FIG. 2a concerns a so called bevel view optic, which comprises essentially an insert funnel 6, a light connection 5 and an optic shank 10 which distally ends in a bevelling 107. Optical systems and light guides are arranged in the bevel view optic in the known manner. Instead of the usual lens system, a picture guide with fibre optics or a videoscope with a distally arranged CCD element may be employed.

Figure 2B:
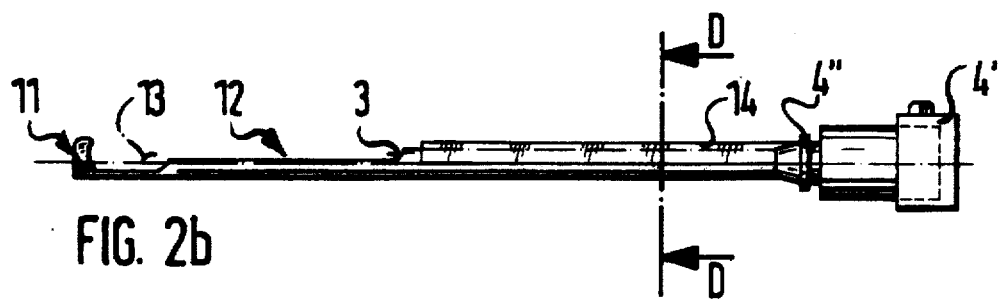
Figure 2C:
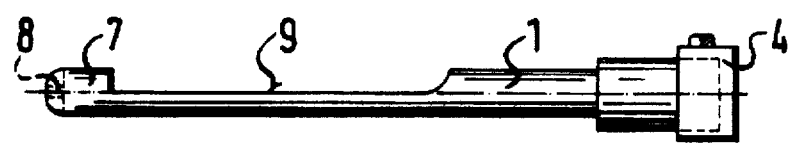

As can be deduced from FIG. 1, with the completed instrument, a cutter 11 of the cutting tool 3 according to FIG. 2b is completely hidden in the distal end of the instrument shank 1, i.e. in its atraumatic rounded end 7.

With the complete assembled instrument the optic shank 10 runs within the tube of the cutting tool 3 and within the instrument shank 1. The exit view of the optic is aligned on the longitudinal slit 9 of the instrument shank 1, so that for example with the optic shown in FIG. 2a, with the completed instrument, it is possible to observe the operation site straight ahead through the distal opening 8 in the instrument shank 1 and laterally through the longitudinal slit 9, whereby the cutter 11 of the cutting tool 3 lies in the field of view of the observation optic 2.

Figure 2D:
Figure 2E:

FIG. 2b shows a lateral view of the cutting tool 3. The tubular shank 15 of this tool in the section at the proximal end of the cutting tool is oval or formed with an oval outer contour by way of a crown 14. FIGS. 2d and 2e represent the cross sections of two different embodiment forms of the tube of the cutting tool in the section plane D—D. At its distal end, the cutting tool 3 comprises at its distal end a cutter or knife blade 11 and, attached to this on the proximal side, longitudinal slits 12, 13, by which means it is ensured that the observation field of the observation optic 2 defined by the longitudinal slit 9 is fully used.

The cutting tool 3 is, as already mentioned, in a first embodiment form according to FIGS. 2b and 2d, provided with a crown 14 in a proximal orbicular section of its shank tube 15, by which means an overall oval shape is achieved in this section. In order to achieve an exact guiding of the observation optic 2 in the shank tube 15 of the cutting tool 3, it is necessary to make the inner cross section of the tube of the cutting tool 3 at least partly orbicular. The oval shape of the outer cross section of the tube of the cutting tool 3 is, as will be further explained, required for the tilting of the cutting tool 3 in the inner space of the instrument shank 1 which has a continuous oval cross section.

FIG. 2e shows a further embodiment form of the cutting tool 3. The required oval outer cross-sectional shape of the tube of the cutting instrument 3 is produced here by drawing a tube with an orbicular cross section, so that the shape of two superimposed incomplete circles arises, whereby the circle 16 again serves the guiding of the optic 2 in the inner space of the tubular shank of the cutting tool.

Figure 3A:
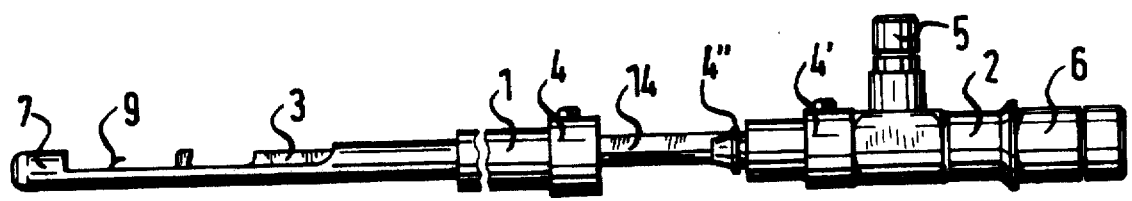
Figure 3B:
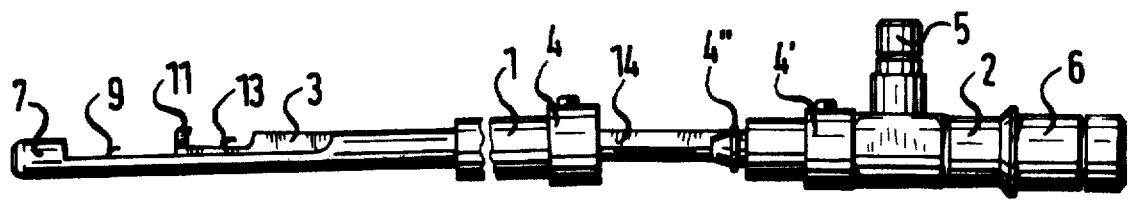

It can be deduced by way of FIGS. 3a and 3b as to how the instrument according to the invention is used. Firstly, with the complete assembled instrument, the locking parts 4, 4" between the instrument shank 1 and the cutting tool 3 are separated. At the same time the locking parts 4' and 4" betweeen the cutting tool 3 and the observation optic 2 remain coupled to one another. The cutting tool 3 with the observation optic 2 fixed thereto can then be moved in the axial direction of the instrument shank 1. With this, for example, a pure observation of the operation site may be carried out. On pulling back the tube of the cutting tool 3 in the proximal direction, the cutter 11 comes out of the distal end 7 of the instrument shank 1 which protects it.

By tilting the rigid tube of the cutting tool 3 as is shown in FIG. 3b, the cutter 11 of the cutting tool 3 is tilted into a position in which the cutter 11 projects beyond the outer diameter of the instrument shank 1. With this, the tilting of the cutting tool 3 may be carried out by one and the same operator, by which means a delicate and tactile cutting operation can be managed. In this position in which the cutting tool 3 is tilted out of the axis of the instrument shank 1, by pulling back the cutting tool 3 and using its blade 11 with the observation optic attached thereto and under constant observation in a so called retrograde operation procedure, the ligament can be severed.

As has already been previously mentioned, by way of the delicate tactile choice of the tilting angle between the cutting tool 3 an the instrument shank 1, the cutting depth may be determined. While doing so it is advantageous that the touch of the operator is exclusively the defining factor for the cutting depth and the cutting procedure.

Figure 4A:
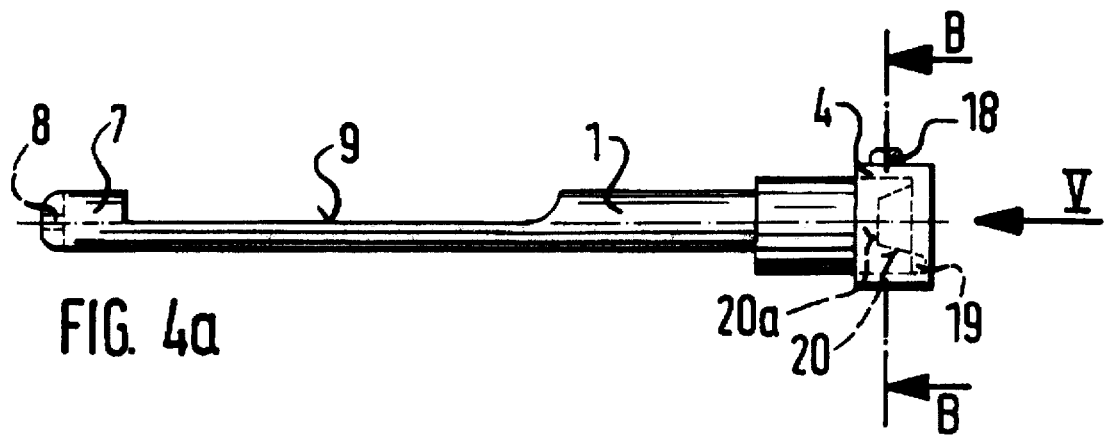
Figure 4B:
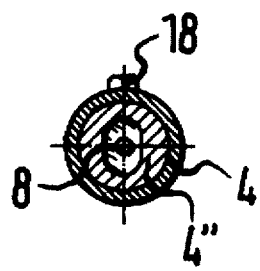
Figure 5:
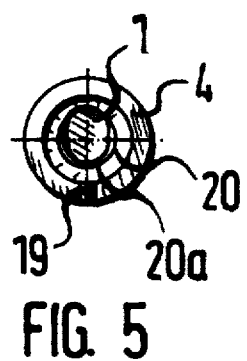

It may be deduced from FIGS. 4a, 4b and 5 as to how the instrument shank 1 is formed, in order to be able to carry out the tilting movement of the cutting tool 3 which is described above. FIG. 4a again shows the instrument shank 1 already described, whereby in this representation the locking part 4 is merely extended by an adjusting nipple 18 and a lug 19 which cooperates in the corresponding locking part 4" with a recess adapted for this purpose and fixes the positioning of the optic and thus the viewing direction thereof.

The locking part 4 comprises, as is shown dashed in FIG. 4a for a conical connection, a conical shaped coaxial recess 20 into which the counterpart 4" of the locking mechanism of the cutting tool 3 fits.

In the sectional representation of FIG. 4b according to the sectional plane B—B of FIG. 4a, the oval cross section of the inner space of the instrument shank 1, parts of the locking mechanisms 4, 4" and also the coaxial exit view window 8 can again be recognized.

By way of both FIGS. 4a and FIG. 4b it is clear that after releasing the connection of the locking parts 4, 4" between the instrument shank 1 and the cutting tool 3 as well as by pulling out the cutting tool 3 together with, where applicable, the observation optic 2 fixed therein, a tilting of the cutting tool 3 out of the axis of the instrument shank 1 is possible. FIG. 5 shows a horizontal projection of the proximal end of the instrument shank 1 or rather of its proximal locking mechanism 4, and one can again here recognize the conical cutout 20 in the locking part 4 as well as an orbicular end 20a of the conical cutout 20.

The handling of the instrument according to the invention for the operation for carpal tunnel syndrome is hereinafter described further. Firstly the instrument is completely assembled in the form as shown in FIG. 1, and the individual parts, like the instrument shank 1, the cutting tool 3 and the observation optic 2 are fixedly attached to one another in a rotationally secure manner with a defined radial arrangement by way of the locking parts 4, 4'. Afterwards the completed instrument is guided to the operation site by way of a small incision. Due to the atraumatically formed distal end 7 of the instrument shank 1, which with the formation of the instrument according to FIG. 1 fully protects the cutter 11 of the cutting tool 3, it is possible to introduce the instrument without an obturator. It is possible that in individual cases dilation must be first be carried out with a dilator.

After the instrument has been correctly placed at the operation site which can already be checked on introduction of the instrument by way of the observation optic, the interface between the cutting tool 3, which for its part is fixed to the instrument shank, and the observation optic 2 is released by releasing the locking part 4'. In this way, in the region of the field of view defined by the shank slit 9 or the distal exit view window 8, it can be checked with the observation optic 2 if and which therapy is required by pushing the observation optic 2 proximally and again in the distal direction.

After the diagnosis has been effected and the operation site has been verified, the observation optic 2 is again rigidly connected with the cutting tool to the locking part 4'. Then by operating the locking part 4, the unit comprising the observation optic 2 and the cutting tool 3 is released from the instrument shank 1. The unit of the observation optic 2 and the cutting tool 3, as has already been described by way of FIGS. 3a and 3b, can be axially adjusted and finally tilted at the desired angle for cutting the ligament.

As has already been mentioned, by tilting, the cutter 11 or the knife blade can project beyond the diameter of the instrument shank 1, and the cutter 11 brought to the ligament. By increasing the tilting more or less, the cutting depth may be set according to requirements. By pulling back the combination of the observation optic and the cutting tool 3 from the instrument shank 1, the ligament may then be severed in a retrograde cutting technique.

When using a fibre optic picture conductor or a CCD system, the whole instrument may be manufactured as a curved system and is adapted better to the anatomy. With such an instrument and also with the instrument represented, the cutter is to be changeably connected to the cutting tool.

What is claimed is:

1. An instrument for endoscopic therapy, adapted for use in therapy of carpal tunnel syndrome, said instrument comprising:

p1a shank tube (1) having an inside with an inner cross-sectional shape having inner dimensions, a length, a longitudinal axis which extends in a longitudinal direction and a longitudinal slit (9) which extends at least over part of the length;

p1a cutting tool (3) having a cutter (11) and being displaceable within said shank tube in the longitudinal direction of the shank tube (1);

p1an observation optic (2) located in the shank tube;

p1means for tilting the cutting tool (3) within the shank tube (1) relative to the longitudinal axis of the shank tube for cutting, the cutter (11) of the cutting tool (3) in a tilted condition extending through the longitudinal slit (9) of the shank tube and projecting beyond an outer diameter of said shank tube; and p1wherein the cutting tool (3) comprises a rigid tube (14, 15, 16, 17) which is longitudinally displaceable inside the shank tube, the rigid tube having a cross-sectional shape and inner and outer dimensions, the cross-sectional shape and the inner dimensions of the rigid tube being adapted to receive the observation optic, the cross-sectional shape and the outer dimensions of the rigid tube being adapted to be received within the inner cross-sectional shape and the inner dimensions of the shank tube (i) such that the rigid tube of the cutting tool (3) together with the cutter (11) can be tilted in the shank tube (1).

2. An instrument according to claim 1, characterized in that the rigid tube of the cutting tool (3) comprises an orbicular outer cross section in a distal section thereof and an oval outer cross section in a proximal section thereof and that the inner cross section of the shank tube is oval.

3. An instrument according to claim 2, characterized in that the oval outer cross section of the rigid tube of the cutting tool (3) in said rigid tube's proximal section is produced by a crown (14), said crown being put on an orbicular outer cross section of the rigid tool tube.

4. An instrument according to claim 1, characterized in that the cutter (11) of the cutting tool (3) is formed as a retrograde cutter (11) at the distal end of said cutting tool.

5. An instrument according to claim 1, characterized in that the cutter (11) is exchangeably attached to the cutting tool (3).

6. An instrument according to claim 1, wherein a second longitudinal slit which forms an opening in the rigid tube is located on a distal section of the rigid tuber the opening being generally alignable with and shorter than the longitudinal slit (9) in the shank tube (1).

* * * * *